United States Patent
Knobbe et al.

(10) Patent No.: US 8,183,053 B1
(45) Date of Patent: May 22, 2012

(54) PRECONCENTRATOR MEDIA AND METHODS FOR PRECONCENTRATION OF AN ANALYTE

(75) Inventors: Edward Thomas Knobbe, Stillwater, OK (US); Mark Fisher, Stillwater, OK (US); Gregory Charles Frye-Mason, Cedar Crest, NM (US)

(73) Assignee: FLIR Systems, Inc., Wilsonville, OR (US)

( * ) Notice: Subject to any disclaimer, the term of this patent is extended or adjusted under 35 U.S.C. 154(b) by 0 days.

(21) Appl. No.: 12/767,351

(22) Filed: Apr. 26, 2010

Related U.S. Application Data

(62) Division of application No. 11/801,325, filed on May 9, 2007, now abandoned.

(60) Provisional application No. 60/799,420, filed on May 9, 2006.

(51) Int. Cl.
*G01N 1/40* (2006.01)

(52) U.S. Cl. .......................... 436/178; 436/177; 436/174

(58) Field of Classification Search .................. None
See application file for complete search history.

(56) References Cited

U.S. PATENT DOCUMENTS

| | | | |
|---|---|---|---|
| 4,805,441 A | 2/1989 | Sides et al. | |
| 5,014,541 A * | 5/1991 | Sides et al. | 73/23.41 |
| 5,109,691 A | 5/1992 | Corrigan et al. | |
| 5,481,110 A | 1/1996 | Krishnaswamy et al. | |
| 6,171,378 B1 | 1/2001 | Manginell et al. | |
| 6,455,003 B1 | 9/2002 | Anvia et al. | |
| 6,764,859 B1 * | 7/2004 | Kreuwel et al. | 436/178 |
| 2005/0095722 A1 | 5/2005 | McGill et al. | |
| 2005/0175702 A1 * | 8/2005 | Muller-Schulte | 424/486 |
| 2006/0153740 A1 | 7/2006 | Sultan et al. | |
| 2007/0084347 A1 | 4/2007 | Boyle et al. | |
| 2007/0180933 A1 | 8/2007 | Grate et al. | |
| 2007/0220953 A1 | 9/2007 | Perry et al. | |
| 2008/0296491 A1 | 12/2008 | Hannigan et al. | |
| 2009/0249958 A1 | 10/2009 | Cambron et al. | |

FOREIGN PATENT DOCUMENTS

| | | |
|---|---|---|
| CA | 1266621 | 3/1990 |
| CA | 2672248 | 6/2008 |
| WO | WO 03101486 A2 * | 12/2003 |
| WO | WO2005/040786 | 5/2005 |
| WO | WO2008/074981 | 6/2008 |
| WO | WO2008/144076 | 11/2008 |

OTHER PUBLICATIONS

Fink, Bruce K. et al. "Functional nanostructures for induction heating: A review of the literature and recommendations for research." Army Research Laboratoy Publication, Nov. 2000.*
Wakamatsu, Hirotake et al. "Preparation and characterization of temperature-responsive magnetite nanoparticles conjugated with N-isopropylacrylamide-based functional copolymer." Journal of Magnetism and Magnetic Materials (2006) 203 327-333.* Karlsson, Karl-Erik. "Separation Efficiency of Slurry-Packed Liquid Chromatography Microcolumns with Very Small Inner Diameters." Analytical Chemistry (1988) 60 1662-1665.*
Muller-Schulte, D. et al. "Novel magnetic microspheres on the basis of poly(vinyl alcohol) as affinity medium for quantative detection of gylcated haemoglobin." Journal of Chromatography A (1995) 711 53-60.*

* cited by examiner

*Primary Examiner* — Yelena G Gakh
*Assistant Examiner* — Christopher A Hixson
(74) *Attorney, Agent, or Firm* — McAfee & Taft

(57) ABSTRACT

The present invention provides improved preconcentrator media suitable for selectively desorbing captured analytes. Additionally, the current invention provides improved methods for concentrating trace quantities of analytes to a degree suitable for detection by a detecting device.

16 Claims, 1 Drawing Sheet

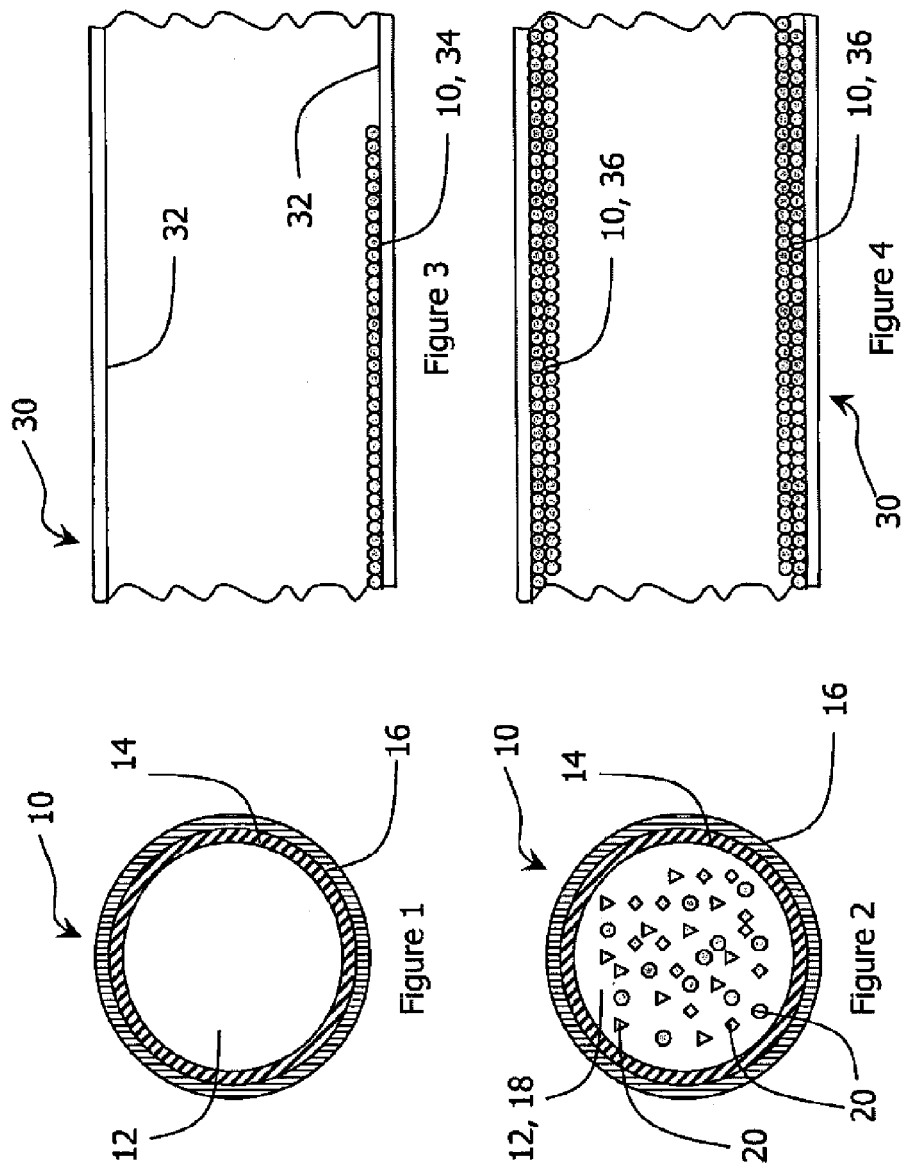

PRECONCENTRATOR MEDIA AND METHODS FOR PRECONCENTRATION OF AN ANALYTE

CROSS-REFERENCE TO RELATED APPLICATIONS

This application is divisional of U.S. patent application Ser. No. 11/801,325 filed May 9, 2007 now abandoned which claims priority to U.S. Patent Application No. 60/799,420 filed May 9, 2006.

BACKGROUND OF THE INVENTION

The current invention is directed to the detection of trace amounts of a target analyte. In particular, the present invention provides preconcentrator media in particulate form suitable for use in a preconcentrator coupled with an analyte detector.

Additionally, the current invention provides methods for preconcentration of an analyte for subsequent detection by a detector. Trace quantities of analytes such as volatile organic compounds, drugs, explosives and other hazardous materials are difficult to detect by conventional techniques. Improving the sensitivity of the detector device is not always practical and can be expensive. Further, conducting such tests outside the laboratory requires the use of portable detectors which frequently are not as sensitive as laboratory based equipment. To overcome these difficulties, preconcentrators have been developed to enhance or increase the concentration of the target analyte in a given volume of a sample for analysis by the detector. While preconcentrators are currently available, they generally rely upon analyte collectors comprising adsorbent material packed into a tube through which the fluid containing the analyte is flowed. However, currently available preconcentrators commonly desorb the analyte from the adsorbent material by application of resistive heating to heat the tube and the adsorbent material to thermally desorb the collected analyte. This design requires high powers and provides relatively slow heating, limiting the concentration enhancement that can be achieved. It is also subject to significant thermal grading affects resulting in overheating and/or non-uniform heating of the adsorbent. Thus, desorption of the analyte is inconsistent and relatively uncontrolled.

The present invention overcomes the difficulties of the prior art by providing preconcentrator media in the form of particles that include heatable cores. As described below, the particles are designed to capture a wide variety of analytes. Additionally, the preconcentrator media of the current invention provides rapid heating, leading to large concentration enhancements, and enhanced control of the desorption process. Thus, use of the preconcentrator media of the current invention enhances the detection of trace analytes.

SUMMARY OF THE INVENTION

In one embodiment, the current invention provides media suitable for use in an analyte preconcentrator. The preconcentrator media is preferably in particulate form and comprises a heatable susceptor core. The core carries at least one coating or shell carried by said core having sorptive characteristics for at least the target analyte(s). Preferably, the core carries a first passivating shell and a second shell having sorptive characteristics for at least the target analyte(s). Preferably the heatable core is a material that can be inductively heated with the heating of the core preferably limited by the Curie point of the core material. Alternatively the heatable core may be a material that absorbs radiation, preferably infrared radiation.

Additionally, the current invention provides a method for concentrating trace levels of analyte to a degree suitable for detection by a detector. The method of the current invention comprises contacting a fluid containing the target analyte(s) with the preconcentrator media. At least a portion of the preconcentrator media has been designed to capture the target analyte(s). In the preferred embodiment, the preconcentrator media is particulate in form. The particles have a heatable core. The core carries at least one coating which has sorptive characteristics for the target analyte(s). Preferably, the core carries a first passivating shell and a second shell having sorptive characteristics for at least the target analyte. Following exposure of the preconcentrator media to the analyte(s) for a period of time sufficient to permit capture of a detectible quantity of analyte(s), the preconcentrator media is subjected to heating of the susceptor core until the temperature of the preconcentrator media increases sufficiently to thermally desorb the analyte. Preferably inductive heating is used to heat the susceptor core and preferably the temperature reached by the heatable core is limited by the Curie point of the core material. Alternatively, exposure to radiation, preferably infrared radiation, absorbed by the heatable core may be used for heating. Prior to heating, the preconcentrator media is brought into the inlet of the detector to be used. Alternatively, a gas is passed over the preconcentrator media during the heating step in a manner which carries the released analyte to the detector.

BRIEF DESCRIPTION OF THE DRAWINGS

FIG. 1 is a depiction of a preconcentrator media particle of the current invention.

FIG. 2 is a depiction of a preconcentrator media particle of the current invention wherein the heatable core includes a heterogeneous dispersion of susceptor core particles.

FIG. 3 depicts a flow channel with a partial monolayer of preconcentrator media supported on the interior wall of the flow channel.

FIG. 4 depicts a flow channel with multiple layers of preconcentrator media supported on the interior walls of the flow channel.

DETAILED DISCLOSURE OF THE PREFERRED EMBODIMENTS

I. Preconcentrator Media

The current invention provides preconcentrator media in particulate form which is suitable for use in a variety of preconcentrator configurations. As known to those skilled in the art, a preconcentrator is used to collect, by absorption or adsorption, trace amounts of an analyte. Collection occurs over a period of time sufficient to yield, upon desorption from the preconcentrator media, an analyte bolus having a concentration suitable for detection by a chemical detector.

The preconcentrator media 10 of the current invention is suitable for use in preconcentrators adapted for both liquid and gaseous phase analyte collection, followed by release of the collected analytes by heating to thermally desorb a gaseous phase of detectible analyte(s). As depicted in FIGS. 1 and 2, preconcentrator media 10 of the current invention is preferably in particulate form, i.e., having a bead or sand like structure. Preferably, particulates 10 of the current invention will have an over-all diameter ranging from about 100 nanometers to about 100 microns. The primary limitation upon the size of the preconcentrator media 10 is the ability to provide sufficient surface area to capture the target analyte while also permitting a satisfactory flow rate through the preconcentrator media 10. Although depicted in the Figs. as round or spherical, particles 10 are not limited to any particular geometric configuration.

In a preferred embodiment, preconcentrator media 10 of the current invention comprises a core 12 that is susceptive to heating. Non-limiting examples of heating would include inductive heating using high frequency electromagnetic fields or heating by absorption of infrared radiation. Thus, when susceptor cores 12, 18 of preconcentrator media 10 are exposed to inductive heat using an induction coil (not shown) that is energized via a high-frequency-modulated electrical current, the resultant high-frequency electromagnetic (EM) field generated by the coil causes localized heating in the inductance susceptor material comprising at least a portion of core 12. The inductance susceptor material may be conductive and/or ferromagnetic/ferrimagnetic in nature with metallic susceptors being primarily heated through the generation of localized eddy currents, while magnetic materials are primarily heated through magnetostrictive hysteresis effects. For the purposes of this disclosure ferromagnetic and ferrimagnetic materials will be referred to generically as magnetic materials. Examples of magnetic materials suitable for use as core 12 of the preconcentrator media include, but are not limited to nickel, cobalt, iron and their associated alloys, magnetite ($Fe_3O_4$), $MnFe_2O_4$, and other iron oxides, and Heusler alloys such as but not limited to MnBi, MnSb, and $Cu_2MnSn$. One advantage of using magnetic materials for inductive heating is that the maximum temperature of the core achieved due to the localized inductive heating can be limited since the dominant inductive heating mechanism stops when the core reaches the Curie temperature and the material loses its magnetic properties.

In another preferred embodiment, preconcentrator media 10 of the current invention comprises a core 12 that absorbs optical radiation, such as infrared radiation. Thus, when preconcentrator media 10 is exposed to radiation at a wavelength that is absorbed, the absorption of the radiation causes localized heating in the susceptor material in core 12.

The current invention further provides susceptor core particles 12 which are tailored to react to different electromagnetic frequencies thereby providing independent heating of one type of particle in the presence of different types of particles. For example, preconcentrator media particles are provided where the size and/or the composition of the susceptor core particles enable them to react to different frequencies of EM fields and/or to different wavelengths of radiation. As will be discussed in further detail below, one set of preconcentration media particles 10 could be heated independently from other sets, enabling selective heating and desorption of analytes collected by different sets of preconcentrator media 10 in a sequential and controlled time-dependent fashion.

Additionally, as depicted in FIG. 2, the current invention provides preconcentrator media particles 10 wherein the core 18 is tailored to react to different radiation wavelengths and/or electromagnetic fields. For example, heterogeneous core 18 comprises dispersions of various sizes and compositions of susceptor material 20. The susceptor material 20 is dispersed within materials such as but not limited to ceramics such as silicates and aluminosilicates, metal oxides such as alumina, zirconia and titania, and organic polymers such as polystyrene, polyethylene, and polypropylene. Susceptor material 20 may be alloys such as iron/nickel alloys which will react to different frequencies of electromagnetic fields. In addition, the maximum temperatures reached during these unique heating stages could be controlled by the distinct Curie temperatures for each alloy. As will be discussed in further detail below, provision of such core particles 18 allows for selective heating and desorption of analytes collected by the preconcentrator media 10 using a temperature staged desorption profile.

Preconcentrator media 10 comprises at least one shell 16 or coat 16 of material carried by core 12, 18. In a preferred embodiment, there are at least two shells 14, 16 or coats. The first coat 14 or shell carried by core 12, 18 is preferably a passivating material which minimizes the interaction of the chemical analytes with the core material. In the preferred embodiment, the second coat or shell 16 is a sorptive coat selected to capture the target analyte. As used herein, the terms shell, coat and coating are used interchangeably. When present, first coat 14 covers a sufficient portion of the susceptor core particle 12, 18 to preclude interaction of the sorptive coat 16 or target analyte(s) with susceptor core particle 12, 18. Second coat 16 carried by core 12, 18 is sufficient to capture the target analyte(s).

Preferably, passivating coat 14 material is non-porous or of low porosity and provides good adhesion to core material 12, 18. Additionally, passivating coat 14 is selected for its ability to bond to second coat 16 carried by core 12, 18. A non-limiting list of materials suitable for use as passivating coat 14 would include metal oxides, silica oxides and aluminosilicates. Suitable metal oxides would include alumina, zirconia and titania. Alternative, materials also suitable for use as the passivating coat include but are not limited to dense low permeability polymers such as polystyrene, polyethylene, polypropylene and polyimides. Finally, metals such as gold, platinum, chromium, and titanium are also suitable for use as passivating coat 14.

Methods for applying passivating coat 14 to core material 12, 18 are well known to those skilled in the art and include, but are not limited to sol-gel processing, deposition from supersaturated solutions, growth due to reaction with active sites formed on the core material surface, and vapor deposition. The thickness of passivating coat 14 may be increased as necessary to adjust the overall size of preconcentrator media particle 10. In particular, the thickness of passivating coat 14 may range from about 10 nanometers to about 10 microns. More preferably, passivating coat 14 will range in thickness from about 200 nanometers to about 1 micron.

A sorptive shell or coat 16 is carried by the susceptor core 12, 18 of preconcentrator media 10. Preferably, sorptive coat 16 is carried by passivating first coat 14. Sorptive shell 16 may be selected to either adsorb or absorb the target analyte as appropriate for the target analyte. Ideally, sorptive coat 16 will provide effective sorption of the desired target analytes, without collection of potentially interfering analytes. Typically, sorptive coating 16 will have a thickness ranging from about 100 nanometers to about 100 microns. More preferably, sorptive coating 16 will have a thickness ranging from about 200 nanometers to about 10 microns.

In general, a porous sorptive coating will be used when the target analyte is best collected by an adsorption process. Analytes of this nature include, but are not limited to chemical warfare agents, toxic industrial chemicals, toxic industrial materials, gases, volatile organic compounds, and semi-volatile organic compounds. When the target analytes are to be collected by adsorption on the surfaces of a porous material, the outer coating material is typically a porous oxide formed using sol-gel chemistry, where the size of the pores may be further controlled using surfactant templated sol-gel processing.

In other example embodiments, the sorptive materials include an iptymer (a porous polymer where the porosity is dictated by internal free volume around large triptycene groups), a porous carbon, a carbon nanotube coating, a metal organic framework material, a porous polymer material, hybrid materials such as organic-inorganic composites, and other similar materials.

Non-porous sorptive coatings are commonly used when the target analyte is selected from the following non-limiting group: low volatility analytes such as explosives and narcotics where release from porous coatings may be too slow.

When the target analytes are to be collected by absorption into the coating material, the outer coating material is typically a polymer material such as a polysiloxane, a polycarbosilane, or an organic polymer such as polyethylene glycol (also called Carbowax), polyisobutylene or polybutadiene.

One skilled in the art will recognize that various modifications of both porous and non-porous materials may be made to incorporate tailored chemical interactions such as hydrogen bonding, polarizability, complexation, or chemisorption, to further enhance the absorption and retention of the target analyte by the outer coating. For example, a large range of polydimethylsiloxanes are commercially available where one or more of the methyl groups are replaced with other chemical moieties, including but not limited to phenyl, cyanopropyl, and perflouroisopropyl groups, that provide tailored chemical interactions to enhance selective absorption into the polymer.

Whether or not sorptive coating 16 is porous or non-porous, the material of sorptive coating 16 is selected for its ability to first collect the target analyte(s) and subsequently, upon heating, to release the analyte of interest in a timely manner and at a reasonable temperature.

Methods for applying the second sorptive coating 16 to passivating coat 14 or core 12, 18 are well known in the art. Examples of suitable processes for applying an adsorptive second coat include, but are not limited to, sol-gel chemistry, including where the size of the pores is controlled using surfactant templated sol-gel processing. Other examples of suitable processes for applying an adsorptive or an absorptive second coat include, but are not limited to deposition from supersaturated solutions, growth due to reaction with active sites formed on the core material surface, and vapor deposition.

II. Methods for Concentrating Trace Levels of an Analyte

The current invention also provides methods for concentrating trace amounts of an analyte or analytes to a degree sufficient for detection by a conventional detector (not shown). The methods of the current invention are suitable for concentrating analytes dispersed in both liquid and gaseous carriers.

In one embodiment, the method of the current invention utilizes a packed bed (not shown) of the preconcentrator media discussed above. This packed bed may entail a section of tubing or other flow channel that is filled with the preconcentrator media to form a set length of the tubing or flow channel packed with the preconcentrator media. Structures to act as physical barriers, such as glass wool, filter materials, or microfabricated structures, may be used to hold the preconcentrator media in place. These materials do not provide any significant sorption of the target analyte(s).

In this embodiment, an analyte dispersed in either a liquid or gaseous carrier flows through the packed bed for a period of time sufficient to permit collection of the analyte by the preconcentrator media. Depending upon the nature of the target analyte, the preconcentrator media will collect the analyte either by adsorption or absorption processes. If more than one target analyte is of interest, the packed bed may consist of a blend or series of preconcentrator media tailored for collection of the different analytes in question.

The time period necessary to permit fluid flow through the preconcentrator media to yield a detectible quantity of analyte is easily calculated by one skilled in the art using the concentration of the analyte in the liquid or gaseous carrier ($C_a$), the flow rate of fluid through the preconcentrator media bed during analyte collection ($V_c$), the flow rate ($V_d$) and peak width ($\tau$) of the analyte bolus during thermal desorption, and the sensitivity of the detector to the target analyte ($C_d$). Using the data and assuming that the collection and desorption efficiencies are near unity, one will be able to determine the sampling time period ($t_s$) necessary to accumulate a detectible amount of analyte as: $t_s=(C_d*V_d*\tau)/(C_a*V_c)$.

Once the predetermined time period has elapsed, flow through the preconcentrator media bed may be terminated or reduced and the preconcentrator media is subjected to heating by exposure to either infrared radiation or to electromagnetic fields that result in inductive heating. For inductive heating of magnetic materials, during exposure to the EM field, the core particles of the preconcentrator media increase in temperature up to the Curie temperature for the material used as the core particle. Once the core particle reaches the Curie temperature further heating is minimal. Preferably, the core material is selected to have a Curie temperature near the desired maximum thermal desorption temperature for the target analyte. In this manner, the method of the current invention controls the desorption of analyte from the preconcentrator media.

The controlled release of analyte from the preconcentrator media substantially increases the concentration of the analyte for detection by a detector (not shown). Preferably, the controlled release of the analyte from the preconcentrator media occurs either in the sample inlet of the detector device or the released analyte is carried by a flowing gas stream, without substantial re-dilution, to the detector device.

In an alternative embodiment, the bed of preconcentrator media in the foregoing method is replaced with at least one and preferably a series of fluid flow channels 30 such as but not limited to gas chromatography columns, glass, metal, or polymeric tubing, microfabricated flow channels, or conventionally machined or milled flow channels. Fluid flow channels 30 support at least a partial monolayer 34 of preconcentrator media particles 10 on interior walls 32. Optionally, flow channels 30 may carry multiple layers 36 of preconcentrator media particles on interior walls 32. In general, when partial monolayer 34 is used, at least thirty percent of interior wall 32 surface will be covered with preconcentrator media particles 10. When a multilayer 36 of preconcentrator media particles 10 are applied to interior walls 32, the surface coverage may exceed one hundred percent of the interior surface area of channel 30, but will be limited to a thickness that does not detrimentally impact fluid flow rate through channel 30.

When using fluid flow channel(s) 30 as support for preconcentrator media 10, fluid carrying the analyte in question is passed through channel(s) 30 thereby allowing the analyte to contact preconcentrator media 10. After a pre-determined period of time for analyte collection, fluid flow through channel 30 is halted or reduced. Optionally, the fluid may be replaced either with an identical carrier gas free of analytes or with a gas stream which is inert to the analyte in question. As the gas is allowed to flow through channel(s) 30, preconcentrator media particles 10 are heated by exposure to infrared radiation or high frequency electromagnetic fields sufficient to heat particles 10 to a temperature sufficient to desorb the analyte from preconcentrator media particles 10. The release of the analyte from preconcentrator media particles 10 occurs over a relatively short period of time thereby yielding a gas containing a significantly greater concentration of analyte than the original concentration of analyte in the initial carrier fluid. The gas carrying the concentrated analyte is subsequently directed to the detector device for determination of the analyte(s) present.

In an alternative embodiment, following the sorption of the analyte onto the preconcentrator media 10, fluid channels 30 may be provided with fluid communication directly to the detector device. Thus, the concentrated analyte is delivered directly to the detector following and during the desorption step.

In another alternative embodiment, the preconcentrator media described herein is embedded in filter media (not shown). The filter media is selected to permit adequate flow of the fluid carrying the target analyte(s). Flow through the filter media necessarily contacts the preconcentrator media. As a result, the preconcentrator media will capture the analyte(s) either through adsorption or absorption on the outer coat of the preconcentrator media particles. After a sufficient period of time, the filter media may be removed from the flowing fluid and placed in a sample chamber suitable for carrying out the desorption step. Preferably, the sample chamber is associated with a detector device suitable for determining the presence of the target analyte(s). Alternatively, the filter media is in fluid communication with the detector device. In this arrangement, the detector device is provided with the ability to pull a gas through the filter media during the heating and thermal desorption thereby delivering the target analyte (s) to the detector.

In yet another embodiment of the current invention, the preconcentrator media particles will preferably comprise a core which is responsive to magnetic fields, such as a magnetic material, which can also be used as the susceptor material for inductive heating. In this embodiment, the preconcentrator media particles are ejected into the fluid and subsequently recaptured by magnetic manipulation. In this method, the sorption step occurs during the convection of the preconcentrator media particles through the fluid. Following collection of the particles by use of a magnet or a magnetic field, the desorption step occurs as discussed above.

Alternatively, the preconcentrator media particles are not ejected or dispersed using magnetic manipulation, but rather the particles are dispersed by any suitable means including manual dispersion over an area where analyte(s) of interest may be present. For example, this could be surfaces of letters, boxes, or other mail and parcels, countertops, floors or doors of facilities, checked or carry on luggage at airports or other transportation terminals, or in the vicinity of the hatchways and doorways of cargo containers and other shipping devices. The preconcentrator media remains for a period of time sufficient to collect any analyte of interest based on diffusion and natural convection transporting the analytes to the sorptive coat of the preconcentrator media particles. Subsequently, the particles are collected either by magnetic manipulation or simply by vacuuming into an appropriate container. Preferably, the container for collection of the preconcentrator media is a sample container suitable for use with a standard detector device that is also capable of performing the thermal desorption step. Following collection, the desorption step is carried out in the manner discussed above. Preferably, the desorption step takes place such that the analyte is released directly into the sample inlet associated with the detector device.

In another alternative embodiment, the preconcentrator media particles are magnetically responsive. These particles are dispersed within a fluid medium and magnetically manipulated into regions of interest to collect target analytes from the fluid. Subsequently, the preconcentrator media particles are gathered magnetically from the fluid into a sample collection chamber. Following collection of the preconcentrator media, the particles are heated to desorb analyte for analysis by a detector device.

In each of the foregoing methods, the preconcentrator media particles are preferably designed to absorb or adsorb the target analytes and to desorb the analytes under controlled conditions. The collection, i.e. absorption or adsorption, preferably takes place on the outer shell of the preconcentrator media. As previously indicated, more than one target analyte may be present in the fluid passing over or through the preconcentrator media. As such, the preconcentrator media may comprise a blend of particles suitable for collecting the various analytes. Alternatively, the outer shell of the preconcentrator media particles may be suitable for collecting more than one specific analyte. In either case, the controlled desorption of the analyte from the preconcentrator media particles will enhance the detection of the analyte by the detector.

As noted above, one means for controlling the desorption of the analyte from the preconcentrator media particle is to select a core material having a Curie temperature near the desired maximum thermal desorption temperature for the analyte. When the core particles reach their Curie temperature, further stimulation by inductive heating using electromagnetic fields will not appreciably increase the heat content of the particle. Thus, core particles may be tuned to a maximum temperature by proper selection of the composition of the core material.

When using preconcentrator media particles 10 to capture a variety of analytes, a variety of preconcentrator media particles 10 having different core compositions responding to different optical wavelengths and/or different EM field frequencies will be used. Thus, application of one wavelength or frequency will yield the release of analyte from particles 10 with one core 12 composition without heating to a temperature which will release different analytes captured by the preconcentrator media 10 with other core 12 compositions. Subsequently, application of a different wavelength or frequency will yield the release or desorption of analytes from particles 10 depending upon the susceptor material forming core 12. By matching the sorptive coatings with the core materials 12, the sequential release of analytes from different sorptive coatings 16 can be achieved using different preconcentrator media particles 10 with tailored core materials 12 and corresponding tailored sorptive coatings.

In embodiments where preconcentrator media 10 comprises a variety of homogenous cores 12, particles 10 carrying outer sorptive shells 16 suitable for collecting different analytes will be coated onto cores 12 of a size and/or material composition that allow them to be heated using different wavelengths or EM field frequencies. In this embodiment, heatable susceptor core materials 12 are selected to respond to different radiation wavelengths or different EM frequencies and, for inductive heating of magnetic core materials 12, may also provide different Curie points. Thus, preconcentrator media particles 10 comprising a variety of homogeneous cores 12 will be capable of collecting several different analytes or analyte classes. The different preconcentrator particles 10 will also provide for the controlled release of the selected analytes or analyte classes when stimulated with different radiation wavelengths or EM field frequencies at controlled intervals. In general, these different sets of preconcentrator media particles 10 will need to be separated from each other, such as by being packed into different sections of a packed bed (not shown), so that heat transfer during heating of one type of preconcentrator particles 10 does not result in heat transfer and desorption from a different type of preconcentrator particle 10.

In another embodiment, the method of the current invention utilizes the preconcentrator media particles 10 depicted in FIG. 2. As noted above such particles comprise a core 18 comprising heterogeneously dispersed materials 20. Such materials 20 may be different magnetic materials or alloys thereof as discussed above. For example, cores 18 may be a blend of nickel, iron, and/or nickel/iron alloy heterogeneously dispersed within ceramics such as silicates and aluminosilicates, metal oxides such as alumina, zirconia and titania, and organic polymers such as polystyrene, polyethylene, and polypropylene to form core 18. Each of these material 20 will have a different Curie temperature point and each will be designed to respond to different frequencies of electromagnetic fields. Additionally, the core material 18 through which the metallic components are dispersed could be designed to respond to infrared radiation. A core particle of this type will have multiple distinct Curie temperatures and will respond to different frequencies of electromagnetic fields and or wavelengths of optical radiation. Accordingly, a preconcentrator media particle 10 of this nature will allow for the collection of a range of different analytes followed by the tailored thermal desorption of these different analytes under a controlled temperature staged desorption process.

The following examples provide a better understanding of the current invention. Preconcentrator media particles having a five-micron diameter magnetite core were covered with inner dense silica passivating layer and an outer porous silica sorptive layer. The passivating and sorptive coatings were applied using sol-gel processing methods followed by a thermal annealing process to ensure that the porosity of the sorptive layer would be stable upon heating during the thermal desorption step. Prior to application of the sorptive coating, the magnetite core particles had a surface area of 6 $m^2/g$ as measured by krypton adsorption and calculated using the BET method. The particles with the sorptive coating were tested by nitrogen adsorption and showed a BET surface area of 55 $m^2/g$. The increase in surface area is due to the porosity of the sorptive coating.

To demonstrate the ability to desorb analyte from the preconcentrator media, the sorptive coated magnetite particles were tested by making a packed bed about one cm in length in a glass thermal desorption tube. Glass wool was used on both ends to hold the particles in place. A laboratory gas chromatograph (GC) with a flame ionization detector (FID) and a solid phase microextraction (SPME) sampler was used to sample the headspace of the analyte to be tested. This method provides the analyte to the preconcentrator media without any added solvent. The thermal desorption tube was placed in line between the injector and the detector of the GC and the analyte samples were injected at an initial temperature of 40° C. Following injection, the GC oven was ramped at 30° C. a minute to a final temperature of 250° C. The time (and corresponding temperature) required for the analyte peak to appear is used to determine the effective retentiveness of the particles being tested. In this instance, three analytes were injected: toluene to simulate a volatile analyte, dimethyl methyl phosphonate (DMMP: a semivolatile nerve agent surrogate), and dimethyl dinitro butane (DMNB, a semivolatile explosive taggant). The preconcentrator media initially adsorbed the analytes and subsequently released them when heated to the appropriate temperature. In these tests, the GC peak corresponding to toluene was recognized at 1:35 min (78° C.), the peak for DMMP at 6 min (220° C.), and the peak for DMNB was just starting to appear at 9 min at 250° C. (max temperature of the run).

Thus, the foregoing example demonstrates the ability of the preconcentrator media to capture and subsequently release analytes in a controlled sequence.

When using the foregoing preconcentrator media in a field application, one would expect to expose the preconcentrator media to a gas containing volatile organics such as toluene for a period of about five seconds to about one minute depending upon the overall volume of the sample area. For example, when testing luggage for volatile components, chemical warfare components or taggants associated with explosives, the preconcentrator media could be dusted over the luggage and collected in less than thirty seconds.

Following collection of the preconcentrator media of the type provided in the foregoing example, the preconcentrator would be placed into the sample inlet of a detector device and heated by inductive or infrared heating. Preconcentrator media having a magnetic core, for example nickel, would be inductively heated by exposure to EM frequencies of about 300 kHz to about 50 MHz for a period of about 0.1 second to about 10 seconds to release volatile organic analytes. We have demonstrated inductive heating of 3 micron diameter nickel particles using alternating EM fields of 7.2 MHz. If chemical warfare analytes or taggants associated with explosives are of interest, the inductive heating periods will be increased to achieve higher thermal desorption temperatures. These preconcentrator media particles will effectively collect chemical warfare agents and release them upon inductive heating to temperatures of 200-250° C. Additionally, these preconcentrator media particles are suitable for collecting explosive taggants such as DMNB and subsequently releasing the analyte upon inductive heating to temperatures of 250-300° C. One skilled in the art will recognize that the EM frequencies and heating periods will vary with the strength of the EM field, the type of susceptor core particles, the sorptive coating and the type of analyte.

Finally, the highest temperature achieved by inductive heating will be controlled by the Curie temperature of the susceptor core composition. In the case of a nickel susceptor core, nickel has a Curie temperature of 354° C., on the high end of typical thermal desorption temperatures. Thus, further heating above 354° C. will be negligible. During heating the analyte is released over a narrow temperature range, generally the majority of a given analyte will be released over a temperature range of 10 to 50° C. and carried to the detector device for analysis. Other core materials can be used to optimize the inductive heating and to tailor the maximum desorption temperature based on the Curie point. Alloys containing nickel, iron or cobalt can be used to obtain Curie points covering the full range of thermal desorption temperatures of interest, from under 50° C. to over 300° C.

Other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

We claim:

1. A method for concentrating analyte for detection by a detector comprising:
   exposing preconcentrator media to a plurality of analytes for a period of time sufficient for said preconcentrator media to capture a quantity of said analyte that will be detectable upon release of said analyte from said preconcentrator media, said preconcentrator media comprising a plurality of particles wherein each particle comprises a heatable core and at least one coating carried by said core wherein said coating is a sorptive coating selected to capture said analyte, wherein said sorptive coating differs from said heatable core, wherein said preconcentrator media has at least a first set and a second set of particles wherein said particles are distinguished by the composition of said heatable core materials;

heating said preconcentrator media to a temperature sufficient to release a detectable concentration of said analyte from said sorptive coating, wherein said step of heating comprises exposing said preconcentrator media to a high frequency electromagnetic field thereby inductively heating said core;

selectively releasing analyte collected by the first set of preconcentrator media particles by inductively heating said preconcentrator media particles and selectively releasing analyte collected by the second set of particles by inductively heating said second set of preconcentrator media particles; and detecting said released analyte using a detector.

2. The method of claim 1, wherein said preconcentrator media is provided as a packed bed and said analyte flows through said packed bed of preconcentrator media.

3. The method of claim 2, further comprising stopping the flow of analyte through said packed bed and subsequently flowing a gas inert to said analyte through said packed bed during said step of inductively heating said packed bed, whereby analyte released from said preconcentrator media is carried to said chemical detector by said gas inert to said analyte.

4. The method of claim 1, wherein said analyte is passed through a passageway and wherein the interior walls of said passageway carry at least a partial monolayer of said preconcentrator media.

5. The method of claim 4, where said particle monolayer covers about 30% of the interior surface area of said passageway.

6. The method of claim 4, wherein the interior walls of said passageway carry multiple layers of said preconcentrator media.

7. The method of claim 1, further comprising the steps of:
dispersing said preconcentrator media over a surface; and,
collecting said media after a period of time sufficient for said media to capture a detectible amount of said analyte.

8. The method of claim 7, further comprising the step of using a magnetic field to collect said media.

9. The method of claim 1, wherein said step of inductive heating comprises exposing said media to a series of differing frequencies of electromagnetic fields.

10. The method of claim 1, further comprising the steps of ejecting said preconcentrator media into a fluidic region containing said analyte and collecting said preconcentrator media using a magnetic field.

11. A method for concentrating analyte for detection by a detector comprising:
providing a first set of preconcentrator media particles and a second set of preconcentrator media particles, each particle comprising an inductively heatable core and a sorptive coating on said core, wherein said inductively heatable core of said first set of preconcentrator media particles is distinguishable from the inductively heatable core of said second set of preconcentrator media particles;

exposing said analyte to said first and second sets of preconcentrator media particles;

selectively releasing analyte from said first set of preconcentrator media particles by selecting a stimulus suitable for inductively heating said core of said first set of preconcentrator media particles to a temperature sufficient to release said analyte from the sorptive coating; and, detecting said analyte using a detector.

12. The method of claim 11, wherein said step of selectively releasing said analyte by selecting a stimulus for inductively heating said core exposes said preconcentrator media particles to electromagnetic radiation.

13. The method of claim 12, further comprising the step of selectively releasing analyte from said second set of preconcentrator media particles by selecting a stimulus suitable for inductively heating said core of said second set of preconcentrator media particles to a temperature sufficient to release said analyte from the sorptive coating; and, detecting said analyte released from said second set of preconcentrator particles using a detector.

14. The method of claim 12, wherein said first and second sets of preconcentrator media particles further comprise a passivating material between said core and said sorptive coating.

15. The method of claim 13, further comprising the steps of:
applying electromagnetic radiation at a first frequency to release analyte from said first set of preconcentrator media particles; and,
applying electromagnetic radiation at a second frequency to release analyte from said second set of preconcentrator media particles.

16. The method of claim 11, wherein said inductively heatable core of said preconcentrator media particles comprises a heterogeneous dispersion of susceptor materials wherein said core experiences inductive heating when exposed to electromagnetic radiation and further comprising:
selectively releasing analyte collected by said preconcentrator media particles by subjecting said preconcentrator media particles to different frequencies of electromagnetic radiation wherein each frequency is selected to induce inductive heating in a specific susceptor material dispersed within said inductively heatable core.

* * * * *